United States Patent [19]

Matsuda et al.

[11] 4,076,747
[45] Feb. 28, 1978

[54] PROCESS FOR HYDRATION OF ACRYLONITRILE TO PRODUCE ACRYLAMIDE

[75] Inventors: Ken Matsuda, Stamford; Kin Hsueh-Yuan Tsu, Norwalk, both of Conn.

[73] Assignee: American Cyanamid Company, Stamford, Conn.

[21] Appl. No.: 696,087

[22] Filed: Jun. 14, 1976

Related U.S. Application Data

[63] Continuation of Ser. No. 558,999, Mar. 17, 1975, abandoned.

[51] Int. Cl.$^2$ ............................................. C07C 102/08
[52] U.S. Cl. ................................................. 260/561 N
[58] Field of Search .................................... 260/561 N

[56] References Cited

U.S. PATENT DOCUMENTS

| 2,421,030 | 5/1947 | Mahan ............................. 260/558 X |
| 3,767,706 | 10/1973 | Habermann et al. ............. 260/561 N |
| 3,804,897 | 4/1974 | Haefele et al. ................... 260/561 N |
| 3,887,425 | 6/1975 | Munch .......................... 260/561 N X |
| 3,956,387 | 5/1976 | Dockner et al. ................. 260/561 N |

Primary Examiner—Arthur P. Demers
Attorney, Agent, or Firm—Gordon L. Hart

[57] ABSTRACT

In the catalytic hydration of acrylonitrile to produce acrylamide by contacting aqueous solution of acrylonitrile with a catalyst, the solubility of acrylonitrile in the aqueous feed solution is increased by presence of acrylamide cosolvent in the feed solution, enabling feed solutions having concentration of acrylonitrile higher than the saturation concentration of acrylonitrile in water without a cosolvent.

1 Claim, No Drawings

PROCESS FOR HYDRATION OF ACRYLONITRILE TO PRODUCE ACRYLAMIDE

This is a continuation, of application Ser. No. 558,999, filed Mar. 17, 1975, now abandoned.

The invention relates to catalytic hydration of acrylonitrile to produce acrylamide.

It is known that acrylonitrile will react with water in contact with any of several solid heterogeneous catalysts to produce acrylamide in very good yield. The selectivity of conversion to acrylamide is near 100% when certain catalysts are used. A variety of solid heterogeneous catalysts for hydration of nitriles have been described, such as manganese dioxide, copper oxide, copper chromium oxide, copper catalysts prepared by reduction of several copper compounds, Raney copper, copper metal in combination with cupric or cuprous ion, and the like.

The present invention relates particularly to continuous acrylonitrile hydration reactions in which a solution of acrylonitrile in water is contacted with a solid heterogeneous catalyst in a continuous catalytic reactor. The catalyst is preferably situated in the reactor as a fixed bed but may be in a fluidized bed, or may be dispersed as a slurry in a stirred continuous reactor. The reactant mixture of water and acrylonitrile is usually fed to the reactor in a single feed stream and it is much preferred to feed the reactants as a homogeneous solution of acrylonitrile in water. A disadvantage is that acrylonitrile is only sparingly soluble in water e.g. 7½% at 25° C., 9% at 60° C., and 12½% at 90° C. Consequently, the product stream from the reactor is a dilute acrylamide aqueous solution.

It was noticed that acrylamide present in the aqueous acrylamide solution acts as a cosolvent which increases the solubility of acrylonitrile. According to the invention the feed solution as fed to a catalytic reactor for hydration of acrylonitrile contains acrylonitrile dissolved to a concentration that is higher than the saturation concentration of acrylonitrile in water alone, by means of acrylamide cosolvent in the solution.

As the acrylamide concentration is increased, in the solvent, the solubility of acrylonitrile is also increased. However, because the presence of acrylamide in the reactor inhibits the conversion of acrylonitrile to acrylamide, there is a practical limit to the advantage that is gained by increasing the acrylonitrile concentration by use of the acrylamide cosolvent. It is preferred to keep the acrylonitrile concentration in the feed solution higher, on a weight percent basis, than the concentration of acrylamide in the feed solution. The practical upper limit of acrylamide concentration in the aqueous product solutions obtained with the invention is found to be in the range from about 20 to about 35% acrylamide.

In the examples which follow, the invention is illustrated by employing product acrylamide to increase the solubility of acrylonitrile in feed streams. The examples describe the invention using staged reactors and using a single reactor. In the latter instance recycled product mixed with the fresh feed provides the acrylamide cosolvent for the feed solution. The catalyst used for the examples are typical preferred catalysts but the invention can be used with any catalyst that is suitable for the hydration reaction.

EXAMPLE 1

Three reactors constructed of one inch diameter stainless steel pipe were placed in series such that a 7% acrylonitrile solution in water is fed to the first reactor. Additional fresh acrylonitrile is mixed with the product of the first reactor and fed to the second reactor. Likewise, additional fresh acrylonitrile is mixed with the product of the second reactor and fed to the third reactor.

A commercially prepared catalyst containing 80% CuO and 17% $Cr_2O_3$ sold under the trade name Harshaw 0203T was crushed and sieved to obtain particles of 40 – 60 mesh size. 30 Gms of the size catalyst was charged to the first reactor, 46 gms to the second and 100 gms to the third reactor. The catalyst in each reactor was reduced by passing a 3% $H_2$ in $N_2$ mixture at 20 liters per minute and 200° C. over the catalyst for 8 hrs.

After reduction, the three reactors together with the associated piping were immersed in a temperature bath maintained at 90° C. Reservoirs of deaerated 7% acrylonitrile solution in water as well as deaerated acrylonitrile were provided and connected to the reactor train through suitable pumps. All liquid streams were maintained under a back pressure of 35 psig.

7% Acrylonitrile solution was fed to the first reactor at a rate of 100 gms/hr. The product from the first reactor contained approximately 0.7% residual acrylonitrile and 8.4% acrylamide. 20 Gms/hr. of acrylonitrile was mixed thoroughly at the bath temperature into the product of reactor 1 and fed to reactor 2. The product from the second reactor contained approximately 5.2% of acrylonitrile and 23.2% acrylamide. 30 Gms/hr. of acrylonitrile was mixed into the product of reactor 2 and fed to reactor 3. The product from reactor 3 contained 14.5% acrylonitrile and 31.5% acrylamide. In each case, the mixed feed to each reactor at the bath temperature was homogeneous and of a single phase. Overall, 62% of the total acrylonitrile fed was converted with greater than 98% selectivity to acrylamide.

EXAMPLE 2

A catalyst commercially available under the trade name BASF R3-11 was crushed and sieved to obtain particles of 40 – 60 mesh size. BASF R3-11 contains 28 – 30% copper combined in copper compounds and dispersed in magnesium silicate.

The reactor system of Example 1 was used. 35, 44 and 96 Gms of the sized catalyst were charged to the first, second and third reactors respectively. The catalyst was reduced as in Example 1.

The temperature bath was maintained at 70° C. 7% Acrylonitrile solution was fed to the first reactor at a rate of 100/gms hr. The product from the first reactor contained approximately 0.3% residual acrylonitrile and 8.9% acrylamide. 15 Gms/hr. of acrylonitrile was mixed in with the product of reactor 1 and fed to reactor 2. The product from the second reactor contained approximately 3.1% acrylonitrile and 21.4% acrylamide. 30 Gms/hr. of acrylonitrile was mixed in with the product of reactor 2 and fed to reactor 3. The final product from reactor 3 contained 11.4% acrylonitrile and 32.4% acrylamide. As in Example 1, the mixed feed to each reactor was of a single phase at the bath temperature. Overall, 68% conversion of the total acrylonitrile feed was converted with greater than 98% selectivity to acrylamide.

EXAMPLE 3

An apparatus was constructed such that a portion of the product from a continuous reactor could be collected and mixed with fresh make up acrylonitrile and water and fed back into the reactor. The apparatus consisted of a feed reservoir, feed pump, reactor maintained in a temperature bath, a product reservoir and transfer lines. The feed and product reservoirs are maintained under a nitrogen atmosphere to exclude air.

123 Gms of Harshaw 0203T catalyst in the form of ⅛ inch × ⅛ inch cylinders was charged as received to a packed bed reactor and reduced. The reactor was maintained at 75° C. In the first pass, deaerated 7% acrylonitrile solution in water was charged to the feed reservoir and fed to the reactor at a rated of 73 gms/hr. The product collected under nitrogen in the product reservoir contained approximately 0.7% residual acrylonitrile and 8.4% acrylamide. A portion of the product was discharged; the remaining portion of the product was transferred back to the empty feed reservoir. For each 1000 gms of product transferred back to the feed reservoir, 97 gms of deaerated acrylonitrile and 70 gms of deaerated distilled water was charged also to the feed reservoir. This new feed for the second pass through the reactor contained approximately 8.9% acrylonitrile and 7.2% acrylamide and was fed to the reactor at a rate of 99 gms/hr. The product collected in the second pass contained approximately 4% residual acrylonitrile and 13.5% acrylamide. In a similar manner, a third pass through the reactor was carried out. For the third pass, the feed contained 8.1% acrylonitrile and 11% acrylamide and was fed to the reactor at a rate of 41 gms/hr. The product from the third pass contained 2.1% residual acrylonitrile and 19% acrylamide.

Although the recycle of product acrylamide was carried out in a batchwise manner for more precise control and therefore a more precise laboratory study, the product could have been recycled and mixed with fresh acrylonitrile feed continuously by the installation of additional metering pumps.

In the foregoing examples the concentration of acrylonitrile in the feed solutions was not the saturation concentration at the solution temperature in every instance, but the actual concentrations of acrylonitrile in the feed solutions were higher in every instance than the maximum concentration of acrylonitrile that could have been dissolved in water without the acrylamide cosolvent.

We claim:

1. In the catalytic hydration of acrylonitrile to product acrylamide wherein an aqueous feed solution of acrylonitrile is contacted in a reactor with a solid heterogeneous catalyst for the hdyration reaction, the improvement wherein the solubility of acrylonitrile in said aqueous feed solution is increased by addition of acrylamide up to about 35% of the feed solution as fed to said reactor as a cosolvent in said feed solution and acrylonitrile is dissolved in said feed solution containing the acrylamide cosolvent in an amount to make an enriched feed solution having acrylonitrile concentration higher than the saturation concentration of acrylonitrile in water without a cosolvent.

* * * * *